United States Patent
Mik (10) Patent No.: US 10,920,260 B2
(45) Date of Patent: Feb. 16, 2021

(54) METHODS AND DEVICES FOR ASSESSMENT OF MITOCHONDRIAL FUNCTION

(75) Inventor: Egbert G. Mik, Rotterdam (NL)

(73) Assignee: Erasmus University Medical Center Rotterdam, Rotterdam (NL)

(*) Notice: Subject to any disclaimer, the term of this patent is extended or adjusted under 35 U.S.C. 154(b) by 320 days.

(21) Appl. No.: 13/059,225

(22) PCT Filed: Aug. 14, 2009

(86) PCT No.: PCT/NL2009/050496
§ 371 (c)(1),
(2), (4) Date: Apr. 1, 2011

(87) PCT Pub. No.: WO2010/019041
PCT Pub. Date: Feb. 18, 2010

(65) Prior Publication Data
US 2011/0182825 A1 Jul. 28, 2011

Related U.S. Application Data (60) Provisional application No. 61/089,349, filed on Aug. 15, 2008.

(51) Int. Cl.
| | | |
|---|---|---|
| A61B 5/00 | (2006.01) |
| A61B 8/00 | (2006.01) |
| A61B 10/00 | (2006.01) |
| C12Q 1/00 | (2006.01) |
| G01N 33/50 | (2006.01) |
| G01N 21/64 | (2006.01) |
| G01N 33/53 | (2006.01) |

(52) U.S. Cl.
CPC ......... *C12Q 1/008* (2013.01); *G01N 21/6408* (2013.01); *G01N 21/6428* (2013.01); *G01N 33/5079* (2013.01); *G01N 33/5302* (2013.01); *G01N 2021/6413* (2013.01); *G01N 2021/6484* (2013.01)

(58) Field of Classification Search
None
See application file for complete search history.

(56) References Cited

U.S. PATENT DOCUMENTS

| 8,008,038 B2 | 8/2011 | Mik et al. |
| 2004/0157905 A1 | 8/2004 | Kennedy et al. |
| 2005/0095456 A1 | 5/2005 | Takeda |
| 2009/0130700 A1 | 5/2009 | Leiden et al. |
| 2010/0241197 A1 | 9/2010 | Chang et al. |

FOREIGN PATENT DOCUMENTS

| EP | 1 742 038 | 6/2005 |
| JP | 2003149152 | 5/2003 |
| WO | WO 93/13403 | 7/1993 |
| WO | WO 01/27585 | 4/2001 |
| WO | WO 07/004873 | 1/2007 |

OTHER PUBLICATIONS

Priebe et al. (Principles of Pressure and Ulcer Management Lin VW, et al. Spinal Cord Medicine: Principles and Practice. New York: Demos Medical Publishing 2003; http://www.ncbi.nlm.nih.gov/books/NBK9252/).*
Sheahan et al. (Physiol. Meas. 1993, 14, 7-12).*
Blood gas tension Wikipedia 2013.*
Brandão et al. (J. Surg. Res. 2003, 110, 235-240).*
Zheng et al. (Oncology Reports 2004, 12, 397-401).*
Mik et al. (Photochem. Photobiol. 2002, 76, 12-21).*
Johannes et al. (J. Appl. Physiol. 2006, 100, 1301-1310).*
Wang et al. (J. R. Soc. Interface 2004, 1, 109-117).*
Aalders et al. (Photochem. Photobiol. 2001, 74, 311-317, abstract).*
Huch et al. (Hops. Pract. 1976, 11, 43-53).*
Krishnamurthy, et al.; Identification of a mammalian mitochondrial porphyrin transprter; Nature; Letters 2006; 10 pages.
Berg, et al, Porphyrin-related photsensitizers for cancer imaging and therapeutic applications: Journal of Microscopy, vol. 218, May 2, 2005, pp. 133-147.
Chantrell et al., "Excited states of protoporphyrin IX dimethyl ester: reaction nfo the triplet with carotenoids." Aug. 26, 1976. pp. 858-865.
Dunphy et al.. "Oxyphor R2 and G2: phosphors for measuring oxygen by oxygen-dependent quenching of phosphorescence," Analytical Biochemistry, 2002. pp. 191-198. vol. 310.
Erickson et al., "Effect of longitudinal oxygen gradients on effectiveness of manipulation of tumor oxygenation$^{1,2}$," Cancer Research, Aug. 1, 2003, pp. 4705-4712, vol. 63.
Ericson, et al, A spectroscopic study of the photobleaching of protoporphyrin IX in solution; Lusers Med. Sci. (2003) 18: 56-62.
European Patent Office Notification for Application No. 06757824.5 dated Jul. 29, 2010.

(Continued)

*Primary Examiner* — Michael G. Hartley
*Assistant Examiner* — Melissa J Perreira
(74) *Attorney, Agent, or Firm* — Thomas|Horsetmeyer, LLP (57) ABSTRACT

Mitochondrial function is measured. Repetitive or continuous measurements are performed of prompt red fluorescence, emerging from the skin due to PpIX build up, and/or delayed fluorescence of PpIX. An estimate of the rate of PpIX generation is used as an indicator of mitochondrial integrity and ATP availability. Mitochondrial oxygen tension is determined from the delayed fluorescence lifetime of PpIX. When blood supply to the measurement volume is interrupted or reduced, the resulting changes to the mitochondrial oxygen tension allow an estimation of information about the kinetics of oxygen consumption in the mitochondria, such as the maximum rate of oxygen consumption as well as the Michaelis-Menten constant, providing information about the oxygen affinity of the mitochondrial respiratory chain.

21 Claims, 3 Drawing Sheets

(56) References Cited

OTHER PUBLICATIONS

European Patent Office Notification for Application No. 06757824.5 dated Oct. 13, 2008.
European Search Report Application No. EP 10 01 2634.1-2204, dated Dec. 7, 2010.
Geissbuehler et al., Triplet imaging of oxygen consumption during the contraction of a single smooth muscle cell (A7r5). Biophysical Journal, Jan. 2010, pp. 339-349. vol. 98.
Hartmann et al., "Non-invasive imaging of tissue $PO_2$ in malignant melanoma of the skin," Melanoma Research, 2006, pp. 479-486, vol. 16, No. 6.
Heyerdahl et al., "Phanncokinetic studies on 5-aminolevulinic acid-induced protoporphyrin IX accumulation in tumours and normal tissues," Cancer Letters, 1997, pp. 225-231, vol. 112.
Hogan, Michael. C., "Phosphorescence quenching method for measurement of intracellular $PO_2$ in isolated skeletal muscle fibers," The American Physiological Society, 1999, pp. 720-724.
Kindig et al., "Effect of extracellular $PO_2$ on the fall in intracellular $PO_2$ in contracting single myoctyes," J. Appl Physiol, Jan. 17, 2003, pp. 1964-1970, vol. 94.
Lo et al., "Calibration of oxygen-dependent quenching of the phosphorescence of Pd-medo-tetra (4-carboxyphenyl) porphine: A phosphor with general application for measuring oxygen concentration in biological systems," Analytica IBiochemcistry, 1996, pp. 153-160, vol. 236, Article No. 0144.
Mik E G et al.. "In vivo mitochondria oxygen tension measured by a delayed fluorescence lifetime technique," Biophysical Journal. Oct. 2008. pp. 3977-3990, vol. 95.
Mik E G et al., "Mitochondrial oxygen tension within the heart." Journal of Molecular and Cellular Cardiology. 2009. pp. 943-951, vol. 46.
Mik E G et al., "Mitochondria $PO_2$ measured by delayed fluorescence of endogenous protophorphyrin IX," Nature Methods Nov. 2006, pp. 939-945, vol. 3, No. 11.
Mik E G et al: "Quantitative determination of localized tissue oxygen concentration in vivo by two-photon excitation phosphorescence lifetime measurements" Journal of Applied Physiology. American Physiological Society 2004, pp. 1962-1969, vol. 97.
Mik et al., Quantitative determination of localized tissue oxygen concentration in vivo by two-photon excitation phosphorescence lifetime measurements, J. Appl. Physiol., 2004, pp. 1962-69, vol. 97.
Patent Abstracts of Japan vol. 2003. No. 09, Sep. 3, 2003 (Sep. 3, 2003) -& JP 2003 149152 A (Igarashi Toshio: Fuji Electric Co Ltd). May 21, 2003 (May 21, 2003).
PCT International Preliminary Report on Patentability for International Application No. PCT/NL2006/000341, dated Jan. 9, 2008.
PCT International Search Report and Written Opinion for International Application No. PCT/NL2006/000341, dated Sep. 11, 2006.
PCT International Search Report, PCT/NL2006/000341, dated Sep. 11, 2006.
Response to European Patent Notification for Application 06757824.5, dated Apr. 22, 2009.
Sinaasappel et al., "Calibration of Pd-prophyrin phosphorescence for oxygen concentration measurements in vivo." The American Physiological Society. 1996. pp. 2297-2303.
Sterenborg et al, "Phosphorescence-fluorescence ration imaging for monitoring the oxygen status during photodynamic therapy." Optics Express, May 3, 2004, pp. 1873-1878. vol. 12. No. 9.
Sterenborg, H J C M et al., "A novel frequency domain fluorescence technique for determination of triplet decay times," Phys. Med Biol, 1999, pp. 1419-1426, vol. 44.
Stummer et al., "In vitro and in vivo porphyrin accumulation by C6 glioma cells after exposure to 5-aminolevulinic acid," Journal of Photochemistry and Photobiology B: Biology, 1998, pp. 160-169, vol. 45.
Submission before oral proceedings and Response to communication dated Jul. 29, 2010 for Application 06757824.5. dated Sep. 28, 2010.
Vanderkool et al., "An optical method for measurement of dioxygen concentration based upon quenching of phosphorescence." The Journal of Biological Chemistry, Apr. 25, 1987, pp. 5476-5482. vol. 262. No. 12.
Vanderkool et al., "Oxygen in mammalian tissue: methods of measurement and affinities of various reactions." The American Physiological Society, 1991, pp. C1131-C1150.
Wilson, et al.; The Oxygen Dependence of Mitochrondrial Oxidative Phosphorylation Measured by a New Optical Method for Measuring Oxygen Concentration: The Journal of Biological Chemistry; Vo. 263, No. 6, Feb. 25, 1983; pp. 2712-2718.
Ziemer et al., "Oxygen distribution in murine tumors: characterization using oxygen-dependent quenching of phosphorescence," The American Physiological Society, 2005, pp. 1503-1510, vol. 98.
Harms et al., Cutaneous respirometry by dynamic measurement of mitochondrial oxygen tension for monitoring mitochondrial function in vivo, Mitochondrion, 2012, http://dx.doi.org/10.1016/j.mito.2012.10.005.
Mik et al., Measuring Mitochondrial Oxygen Tension: From Basic Principles to Application in Humans, Anesthesia & Analygesia, Oct. 2013, pp. 834-46, vol. 117, No. 4.
EP Application 09 788 277.3-2401 Office Action, dated Oct. 18, 2012.
EP Application 09 788 277.3-2401 Office Action, dated Apr. 3, 2012.
EP Application 09 788 277.3-2401 Office Action, dated Jul. 8, 2011.
Response to EP Application 09 788 277.3-2401 Office Action, dated Apr. 21, 2011.
Pressure, Wikipedia, downloaded Mar. 11, 2015 from http://en.wikipedia.org/wiki/Pressure.
Van Bommel et al., Intestinal and Cerebral Oxygenation during Severe Isovolemic Hemodilution and Subsequent Hyperoxic Ventilation in a Pig Model, Anesthesiology, Sep. 2002, pp. 660-670, vol. 97, No. 3.

* cited by examiner

METHODS AND DEVICES FOR ASSESSMENT OF MITOCHONDRIAL FUNCTION

CROSS-REFERENCE TO RELATED APPLICATION(S)

This application is a national entry of PCT International Application Number PCT/NL2009/050496, filed on Aug. 14, 2009, published in English on Feb. 18, 2010 as WO 2010/019041 A1, which itself claims priority under Article 8 of the Patent Cooperation Treaty to U.S. Ser. No. 61/089,349, filed on Aug. 15, 2008.

FIELD OF THE INVENTION

The invention relates to a method and device for assessment of aspects of mitochondrial function.

BACKGROUND

An optical technique for measuring mitochondrial oxygen tension (mitoPOx) is known from EP1742038 and WO 2007/004873 (incorporated herein by reference). See also Mik et al., Nature Methods 3: 939-945, 2006; Mik et al. Biophys. J. 95(8):3977-90, 2008 (incorporated herein by reference). This technique uses the oxygen-dependent optical properties of endogenously synthesized protoporphyrin IX (PpIX), including delayed fluorescence to measure the oxygen-dependent lifetime of the first excited triplet-state ($T_1$) of protoporphyrin IX.

Recently a mammalian mitochondrial porphyrin transporter has been identified, the mitochondrial ATP-binding cassette transporter ABCB6 (see Krishnamurthy et al., Nature 443, 586-589, 2006). This finding indicates that mitochondrial compartmentalization of PpIX precursors and subsequent production of mitochondrial PpIX is dependent on the proper function of ABCB6.

Mitochondria are the energy producing sub cellular organelles. Here energy rich phosphates are produced by the process of oxidative phosphorylation. Inability of the mitochondria to keep up with the cellular energy demand results in cell dysfunction and eventually cell death. Several pathophysiological circumstances are known to lead to mitochondrial dysfunction. Lack of oxygen (anoxia) or reduced oxygen availability (hypoxia) is e.g. detrimental for mitochondrial function. Nitric oxide (NO) is known to compete with oxygen on mitochondrial complex I leading to competitive inhibition of oxygen consumption. Furthermore, bacterial endotoxin is thought to cause mitochondrial swelling and dysfunction by direct action. These are only a few examples of clinically relevant mechanisms of mitochondrial dysfunction.

Despite the undeniable importance of adequate mitochondrial function for sustaining life and the major role of mitochondrial dysfunction in pathophysiology, to date no clinical means of determining specific mitochondrial function at the bedside in human beings exists. This poses heavy constraints on physicians in case of proven (systemic) anaerobic metabolism by for example lactate acidosis. Does the lactate acidosis indicate a lack of oxygen at the tissue level caused by macrocirculatory failure or microcirculatory dysfunction or is it merely an indicator of mitochondrial dysfunction? These are daily questions in the case of treating septic patients, since septic shock evolves from a macrocirculatory collapse into a microcirculatory dysfunction and ultimately to mitochondrial failure. Assessing the state to which a septic syndrome has evolved in a patient upon submission from the ward to the Intensive Care could vastly improve treatment strategy and prognosis making.

Among others it is an object to provide a clinical tool to make an early assessment of mitochondrial function in a subject, preferably in the critically ill patient.

DETAILED DESCRIPTION OF EXEMPLARY EMBODIMENTS

The present technology allows the assessment of several key aspects of mitochondrial function in vivo or in vitro, including mitochondrial integrity, ATP availability, mitochondrial oxygen tension (mitoPO$_2$), oxygen consumption (VO$_2$) and oxygen affinity. This is for instance of utmost importance in biomedical applications, particularly in the field of critical care medicine, where it is necessary to gain insight into the mechanisms of disturbed cellular oxygen availability and oxygen handling.

The technology according to the present invention allows direct and non-destructive measurements of mitochondrial function in cell suspensions, intact tissues and organs in vitro and in vivo and is applicable in humans. The technology relies on the combination of a few novel technologies/findings. These include:

1. A novel optical technique to measure mitochondrial oxygen tension (see Mik et al., Nature Methods 3: 939-945, 2006; Mik et al. Biophys. J. 95(8):3977-90, 2008; patent applications EP1742038 and WO 2007/004873). This technique uses the oxygen-dependent optical properties of endogenous protoporphyrin IX.
2. The recent identification of a mammalian mitochondrial porphyrin transporter, the mitochondrial ATP-binding cassette transporter ABCB6 (Krishnamurthy et al., Nature 443, 586-589, 2006). This finding indicates that mitochondrial compartmentalization of PpIX precursors and subsequent production of mitochondrial PpIX is dependent on the proper function of ABCB6.
3. Although the invention preferably uses the technique depicted under point 1, any existing or future technology that is able to measure PO$_2$ in the mitochondria or in close proximity of the mitochondria (e.g. intracellular) is applicable for part of the invention.
4. The technique depicted under point 1 uses delayed fluorescence to measure the oxygen-dependent lifetime of the first excited triplet-state ($T_1$) of protoporphyrin IX. Other means of measuring this triplet-state lifetime (e.g. the lifetime of transient triplet-triplet absorption) also allow the measurement of oxygen with protoporphyrin IX.
   A) The kinetics of the changes of the lifetime of the first excited triplet state ($TAU_{T1}$) of protoporphyrin IX (or the mitochondrial oxygen tension) after artificially blocking the oxygen supply to the measurement volume provides information about oxygen consumption and oxygen affinity of the mitochondrial respiratory chain/of enzymes in the mitochondrial respiratory chain. Blockage of oxygen supply, e.g. by applying local pressure on the microvessels to temporally occlude them, gradually prolongs $TAU_{T1}$ since mitochondrial oxygen availability drops due to oxygen consumption. The reciprocal triplet-state lifetime ($1/TAU_{T1}$) has a direct quantitative relationship to the mitochondrial $PO_2$ according to the Stern-Volmer relationship. Therefore, the relationship of either $dPO_2/dt$ vs $PO_2$ or $d(1/TAU_{T1}-1/TAU_0)/dt$ vs $(1/TAU_{T1}-1/TAU_0)$ or $d(1/TAU_{T1})$ vs $(1/TAU_{T1})$ allows analysis of the oxygen consumption by Michealis-Menten kinetics. In these equations $TAU_{T1}$ is the measured lifetime of the first excited triplet state (e.g. the delayed fluorescence lifetime) of PpIX and $TAU_0$ is the lifetime of the first excited triplet state under zero oxygen conditions (i.e. a calibration constant). Such analysis provides information on the maximal oxygen consumption ($VO_{2,max}$) and the Michaelis-Menten constant ($P_{50}$). The latter is an indication of the oxygen affinity of the mitochondrial respiratory chain and can be computed as the $PO_2$ (or $1/TAU_{T1}$ or $1/TAU_{T1}-1/TAU_0$) where $VO_2$ is reduced to 50% of the maximum value. $VO_{2,max}$ is an indication of metabolic activity and provides information about functionality of the respiratory chain.

B) Monitoring the rate of emergence of PpIX prompt fluorescence after application of its precursor (5-aminolevulinic acid, ALA) provides information about mitochondrial integrity and ATP availability. PpIX exhibits prompt fluorescence (red light, ~630-710 nm) during photo excitation with blue (~410 nm), green (~510 nm) or red (~632 nm) light. The intensity of prompt fluorescence is linearly dependent on the amount of PpIX as long as excitation intensity is low enough to prevent saturation effects. Therefore the intensity of prompt fluorescence is a direct estimator of PpIX concentration within the measurement volume and the rate of change in prompt fluorescence intensity is a direct estimator of the rate of PpIX buildup in the mitochondria.

This technique is based on the identification of a mammalian mitochondrial porphyrin transporter, the mitochondrial ATP-binding cassette transporter ABCB6. The endogenous substrate of ABCB6 is coproporphyrin III, a precursor of PpIX. The mitochondrial compartmentalization of PpIX precursors and subsequent production of PpIX is therefore dependent on the proper function of ABCB6. ABCB6 is membrane bound and dependent on ATP. Both the integrity of the mitochondrial outer membrane and the adequate production of ATP (directly dependent on mitochondrial function itself) influence the production of PpIX and therefore the emergence of PpIX prompt fluorescence after application of ALA.

ABCB6 is membrane bound and dependent on ATP. Both the integrity of the mitochondrial outer membrane and the adequate production of ATP (directly dependent on mitochondrial function itself) influence the production of PpIX. Diminished mitochondrial integrity due to pathophysiological disorders and a reduced production of ATP by e.g. dysoxia will lead to a reduction in rate of PpIX synthesis. Therefore, monitoring the rate of emergence of PpIX prompt fluorescence after application of its precursor (ALA) provides information about mitochondrial integrity and ATP availability.

In one aspect the invention therefore provides a method of assessment of mitochondrial function and/or mitochondrial integrity in a sample, the method comprising assessment of the rate of porphyrin synthesis after administration of the porphyrin precursor 5-aminolevulinic acid (ALA) to said sample. Said porphyrin preferably comprises protoporphyrin IX or a functional equivalent and/or precursor thereof. A functional equivalent of PpIX is a porphyrin which is formed after administration of ALA to a sample. A precursor of PpIX is a compound which can be processed in vivo leading to the formation of PpIX. When excited, said PpIX or functional equivalent or precursor exhibits luminescence comprising prompt and delayed fluorescence and/or transient absorption as a result of such excitation. Measuring said luminescence and/or transient absorption over time provides information on the amount of said PpIX or functional equivalent or precursor over time. This way, the rate of porphyrin synthesis after administration of ALA is assessed. Further provided is therefore a method of assessment of mitochondrial function and/or mitochondrial integrity in a sample, the method comprising assessment of the rate of porphyrin synthesis after administration of ALA to said sample, wherein porphyrin synthesis is monitored by measuring the rate of production of protoporphyrin IX (PpIX) or a functional equivalent or precursor thereof, wherein said PpIX or functional equivalent or precursor, if excited, exhibits luminescence comprising prompt and delayed fluorescence and/or transient absorption as a result of such excitation. The rate of porphyrin synthesis is preferably assessed by measurement of the mitochondrial PpIX level over time, the method comprising measuring absorption and/or luminescence in a sample caused by an excitation signal, or measuring changes in absorption and/or luminescence in a sample caused by an excitation signal, due to PpIX build up. By "measuring over time" is meant that a measurement is performed at least two different time points, so that a difference in the amount of PpIX (or a functional equivalent or a precursor thereof) over time can be assessed. In one embodiment, repetitive measurements are performed. It is, however, also possible to measure the amount of PpIX (or a functional equivalent or a precursor thereof) continuously. Either way, a difference in amount over time and, hence, the rate of porphyrin synthesis, is assessed.

In a particularly preferred embodiment a method according to the invention is provided, wherein said measurement over time comprises:

repetitive or continuous measurements of the intensity of prompt red fluorescence caused by an excitation signal, the prompt red fluorescence emerging from the sample due to PpIX build up; and estimation of the rate of PpIX generation and using the rate as an indicator of mitochondrial integrity and/or ATP availability. Prompt fluorescence is preferably measured by detecting the fluorescence signal during, or in phase with, photo excitation at one of the PpIX absorption bands.

Said sample preferably comprises a tissue sample. More preferably, said sample comprises skin tissue. This allows assessment of mitochondrial function and/or mitochondrial integrity at the bedside in human beings.

We described a method to measure quantitatively mitochondrial $PO_2$ in living cells by oxygen-dependent quenching of the delayed fluorescence lifetime of PpIX (Nature Methods 3, 939-945, 2006). This method is not limited to cultured cells, but can also be applied in vivo (Mik et al., Biophys J 95(8):3977-90, 2008; Mik et al. J Mol Cell Cardiol 46(6):943-51, 2009; patent applications EP1742038 and WO 2007/004873). The absolute value of mitochondrial $PO_2$ is an important physiological parameter indicating mitochondrial oxygen availability. According to the present invention, measurement of the kinetics of delayed fluorescence lifetime (indicative of changes in mitochondrial $PO_2$) after artificially blocking the oxygen supply is now used to provide additional information about oxygen consumption and oxygen affinity of the mitochondrial respiratory chain and, hence, about mitochondrial functioning. Blockage of oxygen supply, e.g. by applying local pressure on the microvessels to temporally occlude them, will gradually prolong the delayed fluorescence lifetime since mitochondrial oxygen availability drops due to oxygen consumption. Even without calibration of the delayed fluorescence signal, the reciprocal lifetime (1/TAU) will have a direct quantitative relationship to the mitochondrial $PO_2$ according to the Stern-Volmer relationship. The faster the delayed fluorescence lifetime is prolonged, the more oxygen is consumed. If oxygen consumption is within normal limits, this aspect of mitochondrial functioning is regarded as normal. Oxygen consumption well above normal values indicates mitochondrial uncoupling and, hence, suboptimal functioning. Vice versa, if the delayed fluorescence lifetime appears to prolong very slowly, it demonstrates that mitochondrial oxygen consumption is low. In such case, it is concluded that the mitochondria do not function properly.

A method according to the invention is not limited to oxygen consumption, since consumption of other metabolic substrates can also be measured in order to assess mitochondrial function. Further provided is therefore a method of assessment of mitochondrial function in a sample, the method comprising:

restricting or ceasing the supply of oxygen and/or other metabolic substrates to said sample;

repetitively or continuously measuring a parameter indicative for the kinetics of the mitochondrial respiratory chain;

estimating the rate of change of said parameter; and using said rate as an indicator of consumption of said metabolic substrate and affinity of the mitochondrial respiratory chain for said metabolic substrate.

In one preferred embodiment said parameter is mitochondrial oxygen tension. Moreover, the measured value is preferably related to optical properties of PpIX, most preferably to the triplet-state lifetime. The invention therefore provides a method of assessment of mitochondrial function in a sample, the method comprising:
restricting or ceasing oxygen supply to said sample;
repetitively or continuously providing an excitation signal to PpIX present in said sample;
repetitively or continuously measuring the lifetime of the first excited triplet state ($TAU_{T1}$) of Pp IX or its transient;
estimating the rate of extension of said lifetime; and
using said rate as an indicator of oxygen consumption and oxygen affinity of the mitochondrial respiratory chain. Again, said sample preferably comprises a tissue sample, more preferably skin tissue in order to allow assessment of mitochondrial function and/or mitochondrial integrity at the bedside in human beings.

Example Applications

The technology allows, for example, measurement of mitochondrial function in the skin after topical application of ALA in the form of e.g. ALA-gel, ALA-cream or ALA-ointment. After application repetitive or continuous measurements of the prompt red fluorescence emerging from the skin due to PpIX build up allows estimation of the rate of PpIX generation, an indicator of mitochondrial integrity and ATP availability (according to B). In order to diminish the influence of skin temperature, skin temperature is preferably regulated by e.g. a heating pad (keeping the temperature fixed to a value typically in the range of 35-44° C.). Prompt fluorescence is preferably measured by detecting the fluorescence signal during (or in phase with) photo excitation at one of the PpIX absorption bands (e.g. around 410 nm, 510 nm or 634 nm). The excitation light source can be any light source capable of generating such light in continuous, modulated or pulsed fashion. Examples include a xenon light source with bandpass filter or monochromator, light emitting diodes (LEDs) and several types of laser systems (e.g. diode lasers and tunable lasers). The detector can be any sensitive photodetector like a photodiode, avalanche photodiode, photomultiplier tube, charge coupled device (CCD camera) with or without image intensifier. Detection systems may comprise phase-locked detection techniques in order to improve signal-to-noise ratio.

Further provided is therefore a device for measurement of mitochondrial function, the device comprising:

a light detector arranged to detect fluorescence or other luminescence from the sample volume; and a control unit configured to obtain repetitive or continuous measurements of prompt red fluorescence emerging from the sample due to PpIX build up, to estimate a rate of PpIX generation, and to use the rate as an indicator of mitochondrial integrity and ATP availability. Said device preferably further comprises an excitation light source directed to illuminate a sample volume.

A device according to the invention is preferably capable of measuring values related to optical properties of PpIX, such as the triplet-state lifetime, to be able to determine mitochondrial oxygen tension.

Figure 1:
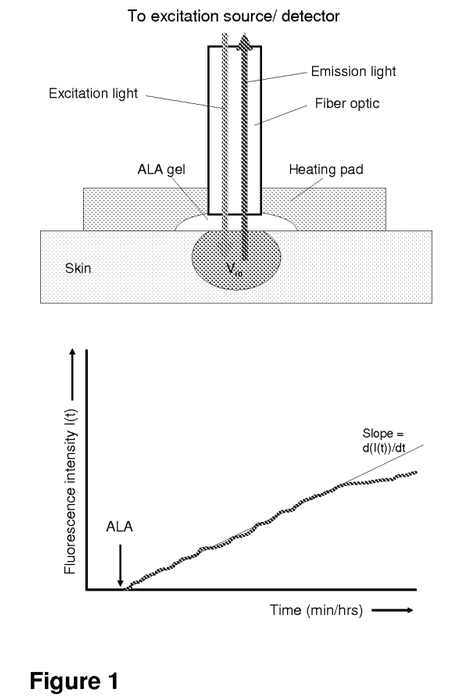
FIG. 1: shows detection of prompt fluorescence after 5-aminolevulinic acid (ALA) administration over time.

FIG. 1 is a non-limiting schematic overview showing the principle of detection of prompt fluorescence of protoporphyrin IX (PpIX) in response to the incidence of excitation light (e.g., blue light of e.g. 405 nm) on a sample such as for instance a volume of skin or other tissue in vivo or in vitro. Measurements are preferably performed with a detector or an optical fiber connected to a detector or a system of lenses, filters and/or mirrors that projects an image of a part of the measurement volume onto a detector. If an optical fiber is used it is preferably positioned with one end facing the measurement sample, in contact or not, and the other end towards a detector. Administration of 5-aminolevulinic acid (ALA) to the sample (topically or systemically) results in uptake of ALA in the cells, where the increased concentration of ALA leads to an increase in the rate of production of PpIX and ultimately to a buildup of the concentration of PpIX in the mitochondria, resulting in an increased fluorescence intensity. Repeated measurements of the intensity, preferably quantitative measurements, at different time points (or continuous measurement over time) provide an assessment of the rate of emergence of prompt fluorescence, the time until first detection as well as the level of saturation and the time to achieve it as well as the shape of the curve as the saturation is approached.

To increase the accuracy and significance of the measurements and in order to reduce the influence of other variables, a measurement is preferably performed under specified and controlled conditions. Such conditions preferably include temperature, at least the temperature in the measurement volume (in vivo preferably a little higher than normal but preferably lower than 42° C., most preferably around 35-40° C. for skin. For in vitro samples this also includes temperature regulation of a sample and preferably its surroundings (in order to minimize temperature gradients)).

Said controlled conditions preferably also include pressure onto a sample and/or the supply of oxygen and nutrients, and/or ambient light conditions (preferably shielded from ambient light). Conditions also preferably include specified administration form of ALA, including a specified concentration and/or composition and/or temperature and/or quantity per surface area and/or volume of the sample and/or temperature of ALA. ALA is preferably administered topically onto the surface of the measurement volume or locally injected into it, preferably in the form of a gel or liquid solution. In one embodiment ALA is systemically administered into the body of a subject. Systemic administration can for instance be in the form of intravenous injection, intraperitoneal injection or oral administration. For surface administration, the surface is preferably prepared (e.g., cleaned or primed with certain substances such as lipids or hydrophilic gel) in order to create a standard acidity, water and lipid content and composition on the surface of or within the sample and in order to allow the ALA to spread at a predictable rate and in a predictable manner through the sample.

The delayed fluorescence lifetime of the PpIX signal can be used to measure the mitochondrial $PO_2$ in the skin and the response of the mitochondrial $PO_2$ to cessation of oxygen supply to the measurement volume ($V_m$). The latter can be induced by e.g. applying local pressure on the skin in order to occlude the small arterioles and veins and the capillary bed. This will stop the convective flow of oxygen into the measurement volume and allows the observation of oxygen consumption kinetics. An example in which the pressure is applied directly by the excitation/emission optics is provided in FIG. 2.

Figure 2:
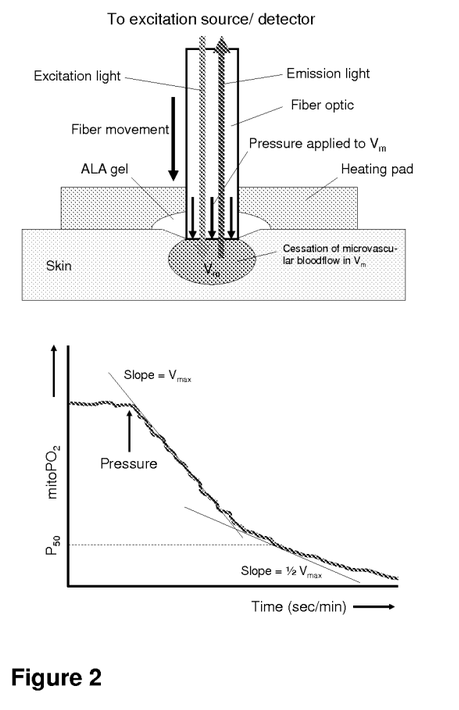
FIG. 2: shows measurement of mitoPO$_2$ kinetics after cessation of oxygen supply.

FIG. 2 shows measurement of $mitoPO_2$ kinetics after cessation or reduction of oxygen supply. In one embodiment an external pressure exerted by a movable fiberoptic member is used to stop microvascular blood flow, which has the advantage of being able to measure with the same instrument that exerts the pressure. It will be understood by those skilled in the art that other methods can be used to exert pressure on the sample and/or that other methods than pressure on arterial or venous capillaries can be used to stop the supply of oxygen and/or nutrients to the sample (e.g., stopping external supply or exchanging liquids in the case of tissue engineering, or stopping the flow in the major arteries supplying a region of interest with external pressure or catheter balloon or clamps, or drug agents that constrict arteries or arterial capillaries). Further provided is therefore a method according to the invention, wherein the sample comprises in vivo skin or organ tissue and wherein oxygen supply to a measurement volume is restricted or reduced by outside pressure of the sample higher than the venous capillary closing pressure (typically higher than 8-12 mmHg in skin tissue in humans) but lower than arterial capillary closing pressure (typically lower than 30-40 mmHg in skin tissue in humans) to impede return flow. Alternatively, oxygen supply to a measurement volume is in one embodiment restricted or reduced by outside pressure applied to a region including or surrounding the measurement volume higher than arterial capillary closing pressure (typically higher than 30-40 mmHg in skin tissue in humans).

The delayed fluorescence is in one embodiment measured in the time domain (i.e. measuring the decay of the delayed fluorescence after a pulse of excitation light). Alternatively, the delayed fluorescence is measured in the frequency domain (i.e. measuring the phase shift between the modulated excitation light and the delayed fluorescence emission). Alternatively, instead of delayed fluorescence, other means to measure $TAU_{T1}$, e.g. triplet-triplet absorption, is employed, either in the time domain or the frequency domain. In the time domain, excitation sources are typically flash-lamps or pulsed laser systems and in the frequency domain any modulated light source with appropriate wavelength of light emission (e.g. modulated diode lasers or modulated LEDs) are feasible. The detector can be any sensitive photodetector like a photodiode, avalanche photodiode, (gated) photomultiplier tube, charge coupled device (CCD camera) with or without image intensifier. Detection systems may comprise phase-locked detection techniques in order to improve signal-to-noise ratio. To achieve adequate signal-to-noise ratios the technique works best in a dim to dark surrounding.

Further provided is therefore a device for measurement of mitochondrial function, the device comprising:

an excitation light source directed to illuminate a sample volume;

a light detector arranged to detect fluorescence or other luminescence from the sample volume or absorption by the sample volume; and a control unit configured to obtain repetitive or continuous measurements of mitochondrial oxygen tension, and to use the measurements after a reduction in oxygen supply as an indicator of the kinetics of the mitochondrial respiratory chain.

As said before, a device according to the invention is preferably capable of measuring values related to optical properties of PpIX, such as the triplet-state lifetime, to be able to determine mitochondrial oxygen tension.

One particularly preferred embodiment provides a device according to the invention, comprising:

an excitation light source directed to illuminate a sample volume;

a light detector arranged to detect fluorescence from the sample volume; and a control unit configured to obtain repetitive or continuous measurements of delayed fluorescence, and to use the measurements after a reduction in oxygen supply as an indicator of oxygen consumption and oxygen affinity of the mitochondrial respiratory chain. The control unit is preferably configured to use the measurements after a reduction in oxygen supply to deduce the Michaelis-Menten constant and the maximal oxygen consumption.

As explained before, a device according to the invention preferably comprises a heating pad and/or a thermometer and/or algorithms for correcting for sample temperature or changes thereof. Moreover, a device according to the invention preferably comprises a pressure pad for applying local pressure on tissue containing arterioles, veins and/or the capillary bed that supply oxygen to the sample volume. Heating and/or pressure may be applied by the same unit. Hence, said heating pad and/or thermometer and/or pressure pad may be integrated in a single unit.

In conclusion, the present invention provides the insight that measuring kinetics of prompt PpIX fluorescence after ALA administration is suitable to determine mitochondrial outer membrane integrity and intracellular ATP availability in vivo and that the transition of measuring static delayed fluorescence lifetimes to transient changes in delayed fluorescence lifetime is suitable to determine Michaelis-Menten kinetics of the mitochondrial respiratory chain and the interpretation.

The combination of time resolved prompt fluorescence intensity measurements and delayed fluorescence lifetime measurements of ALA enhanced protoporphyrin IX is particularly suitable for comprehensively assessing mitochondrial integrity, ATP availability, oxygenation and respiration.

The time course of changes in reciprocal lifetime of PpIX delayed fluorescence after occlusion of oxygen supply is used to assess the Michaelis-Menten kinetics of the mitochondrial respiratory chain.

The time course of PpIX prompt fluorescence after administration of ALA is measured and used as an indication of mitochondrial ATP availability/production.

Now that the present invention has provided the above mentioned insight, the combination of mitochondrial $PO_2$, $VO_{2,max}$ and $P_{50}$ is preferably used to differentiate between disorders of oxygen supply or oxygen utilization. Different disorders often result in different values of these parameters. Hence, when these parameters are compared to values at other times or in other individuals (healthy or with specific conditions) information will be obtained about the nature of an individual's disorder. Information is also obtained when the relations between the above mentioned parameters are compared. For instance, partial blockage or dysfunction of the respiratory chain (e.g. by toxins) will lead to a reduction of $VO_{2,max}$. Contrary, uncoupling of the mitochondrial respiratory chain (e.g. by disruption of the integrity of the mitochondrial inner membrane) will lead to an increase in $VO_{2,max}$. Hence, measurement of $VO_{2,max}$ provides valuable information about the underlying cause of disease. Moreover, in case of a reduced $VO_{2,max}$, $P_{50}$ is indicative of the mechanism by which the oxygen consumption (and therefore the mitochondrial function) is reduced. For example, competitive inhibition by nitric oxide will cause an increase in $P_{50}$, while non-competitive inhibition by toxins will reduce $VO_{2,max}$ without altering $P_{50}$ significantly.

Potential clinical en preclinical applications include use in the ICU (Intensive Care Unit). The following is a (non comprehensive) list of possible applications:

Diagnosis and management of systemic inflammatory response syndrome and sepsis.

Diagnosis and management of mitochondrial disorders such as for instance mitochondrial myopathies, leber hereditary optic neuropathy (LHON), Leigh syndrome, neuropathy/ataxia/retinitis pigmentosa/ptosis (NARP), and/or myoneurogenic gastrointestinal encephalopathy (MNGIE), especially in neonates.

Tumor diagnosis and therapy (e.g. photodynamic therapy).

Evaluation of fluid therapy.

Evaluation of oxygen carrying resuscitation solutions.

Preservation of organs for transplantation.

Fundamental research to oxygen transport to tissue.

Perioperative use in major surgery: heart, tube-stomach etc.

Tissue engineering.

Care, revalidation, and screening or distinction of tissue type and function.

Management and guidance of training, sports and exercise

Engineering of tissue.

Monitoring growth and selection of organisms including animals plants or fungi.

Monitoring and control of processes, e.g. in biochemical reactors.

The technical advantage in all those fields lies in the fact that it is made possible to monitor oxygen and oxygen utilization and functioning on the level in the tissue where it is most important: in the mitochondria. Since the mitochondria play a major role in ischemia-reperfusion injury encountered in e.g. reperfusion of transplanted organs, the technique will provide new insights in the pathophysiology of transplantation failure. The effects of fluid resuscitation on blood pressure and macrocirculatory parameters are nowadays easily measured. However, the effect on tissue oxygenation and function are less well known. Here the technique may be used in (pre)clinical research and as a clinical monitoring tool. With the advance of tissue engineering techniques and larger tissue parts being created, the oxygen supply becomes a limiting factor. The invention may also be used as a research tool in this field of research.

Example 1

Figure 3:
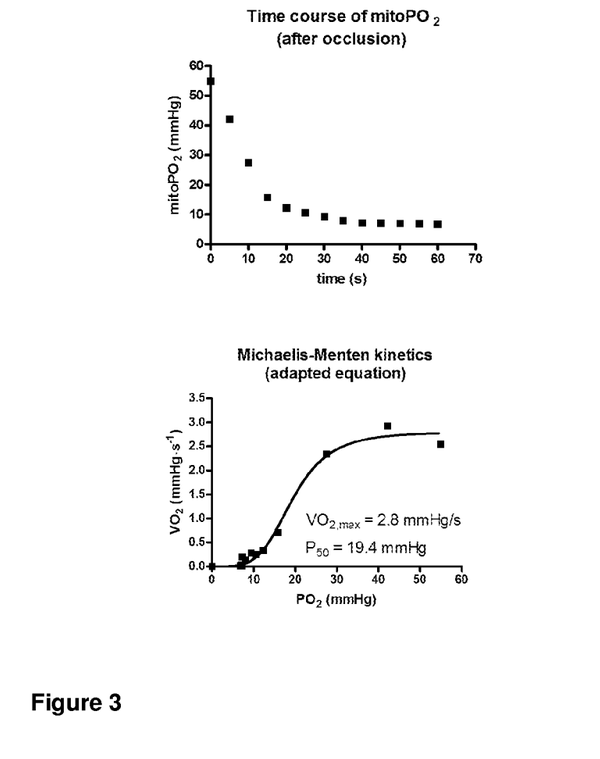
FIG. 3: shows results of an actual measurement of mitochondrial PO$_2$ kinetics in the skin of the hind limb of a rat.

FIG. 3 shows results of an actual measurement of mitochondrial $PO_2$ kinetics in the skin of the hind limb of a rat. In this case ALA was intravenously administrated in a dosage of 200 mg/kg. Measurements were performed 2 hours after ALA administration. MitoPO2 was measured at regular intervals of 5 seconds using a time-domain based setup consisting of a tuneable pulsed lasersystem tuned at 510 nm and a cooled microchannelplate photomultiplier tube detecting delayed fluorescence at 690 nm. Delayed fluorescence lifetimes were obtained by monoexponential fitting of the delayed fluorescence traces. Conversion to mitoPO2 values was performed with the Stern-Volmer relationship and assuming that previously determined quenching constants for liver tissue (Mik et al., Biophysical J 95(8):3977-90) are also applicable for the skin. The Stern-Volmer relationship gives the linear relationship between reciprocal lifetime and mitoPO2 value, i.e. $mitoPO_2=(1/TAU-1/TAU_0)/k_q$ where TAU is the measured delayed fluorescence lifetime, $TAU_0$ is the delayed fluorescence lifetime under zero oxygen conditions and $k_q$ is the quenching constant. In this example we used $TAU_0$=0.8 ms and $k_q$=830 $mmHg^{-1}$ $s^{-1}$. (as described in Mik et al., Biophysical J 95(8):3977-90) The second panel ($VO_2$ vs $PO_2$) is constructed by determining the slope ($dPO_2/dt$) of each measurement point in the first panel. $VO_2$ is expressed as mmHg $s^{-1}$ and is in fact a "surrogate" for true oxygen consumption, which is usually measured in absolute values like micromole $O_2$/min. In our example this is not possible because the exact measurement volume is not known, but the "surrogate" $VO_2$ can be used in the classical way and provides all clinically relevant information. Interestingly it is to note that $VO_2$=0 mmHg $s^{-1}$ at mitoPO2>0 and this is not according to classical Michaelis-Menten kinetics. This discrepancy might be due to in vivo regulation of metabolism not accounted for by classical Michaelis-Menten kinetics or by erroneously assuming calibration in liver to be valid in the skin in the calibration constants. A convenient way to correct for this is by using an adapted Michaelis-Menten equation for fitting of the data in order to retrieve $VO_{2,max}$ and $P_{50}$.

Adapted equation (Michaelis/Boltzmann):

$$VO_2=VO_{2,max}((PO_2/P_{50})^n)/(1+((PO_2/P_{50})^n))$$

where $VO_2$ is the oxygen consumption, $VO_{2,max}$ is the maximal oxygen consumption, $P_{50}$ is the $PO_2$ value at which $VO_2=VO_{2,max}/2$ and n is a power constant. Fitting on the data occurs with the constrains $VO_{2,max}$, $P_{50}$ and n all >=0.

An alternative approach would be to subtract the $PO_2$ value at which $VO_2$ becomes zero as a kind of baseline correction, but this approach might be less generally applicable. Therefore, the use of the Michaelis/Boltzmann equation is preferable. This approach is useful in clinical practice and shows a method of how one skilled in the art can easily obtain the values for $VO_{2,max}$ and $P_{50}$ in vivo.

The invention claimed is:

1. A non-invasive method of measuring the lifetime of the first excited triplet-state (TAUT1) of endogenous protoporphyrin IX (PpIX) ex vivo or in vivo in mitochondria in cells in a sample volume of skin tissue of a subject, the method comprising:

administering 5-aminolevulinic acid to the skin cells in said sample volume;

repetitively or continuously measuring fluorescence of protoporphyrin IX (PpIX) in mitochondria in the skin cells in said sample volume of skin tissue, using a device comprising an excitation light source directed to illuminate said sample volume, a light detector arranged to detect fluorescence from said sample volume, and a pressure pad for applying local pressure on said sample volume;

restricting or ceasing the supply of oxygen to the cells in said sample volume of skin tissue by applying local, positive pressure on the tissue to thereby occlude microvessels comprised in said said sample volume of skin;

repetitively or continuously measuring the lifetime of the first excited triplet state (TAUT1) of endogenous protoporphyrin IX (PpIX) in mitochondria in cells in said sample volume of skin tissue using said device, whereby at least two measurements are performed during said restricting or ceasing the supply of oxygen to the cells in said sample volume of skin tissue;

discontinuing applying local, positive pressure to said sample volume of skin tissue through said pressure pad to thereby discontinue said restricting or ceasing the supply of oxygen to the cells in said sample volume of skin tissue; and repetitively or continuously measuring the lifetime of the first excited triplet state (TAUT1) of endogenous protoporphyrin IX (PpIX) in mitochondria in cells in said sample volume of skin tissue.

2. The method according to claim 1, wherein multiple measurements of the lifetime of the first excited triplet state (TAUT1) of endogenous protoporphyrin IX (PpIX) in mitochondria in cells in said sample volume of skin tissue are performed to provide information on the maximal oxygen consumption $VO_{2,max}$ and/or the Michaelis-Menten constant $P_{50}$ of the mitochondrial respiratory chain in said cells in said sample volume of skin tissue.

3. The method according to claim 1, wherein the tissue comprises in vivo skin or organ tissue and wherein oxygen supply to a measurement volume is restricted or reduced by outside pressure on the tissue higher than the venous capillary closing pressure but lower than arterial capillary closing pressure to impede return flow.

4. The method according to claim 1, wherein oxygen supply to a sample volume is restricted or reduced by outside pressure applied to a region including or surrounding the sample volume higher than arterial capillary closing pressure.

5. The method according to claim 2, wherein the same instrument is used for the exertion of local pressure on the microvessels of the tissue and the measurement of the lifetime of the first excited triplet state (TAUT1) of PpIX.

6. The method according to claim 2, wherein the measurement of the lifetime of the first excited triplet state (TAUT1) of PpIX is performed with an instrument that comprises at least one measuring unit selected from the group consisting of a detector; an optical fiber connected to a detector; and a system composed of at least one of lenses, filters and mirrors that projects an image of a part of the measurement volume onto a detector; and wherein the same instrument is used for the exertion of local pressure on the microvessels of said tissue.

7. The method according to claim 1, wherein said pressure pad is a movable fiberoptic member, and wherein the measurement is carried out with said fiberoptic member.

8. The method according to claim 1, wherein repetitively or continuously measuring comprises repetitively or continuously providing an excitation signal to protoporphyrin IX (PpIX) present in the tissue comprising the occluded microvessels.

9. The method according to claim 2, wherein the combination of mitochondrial oxygen consumption, $VO_{2,max}$ and $P_{50}$ is used to differentiate between disorders of oxygen supply and oxygen utilization.

10. The method according to claim 9, wherein a reduction of $VO_{2,max}$ compared to values at other times or in healthy individuals is associated with partial blockage or dysfunction of the mitochondrial respiratory chain.

11. The method according to claim 9, wherein an increase in $VO_{2,max}$ compared to values at other times or in healthy individuals is associated with uncoupling of the mitochondrial respiratory chain.

12. The method according to claim 10, wherein said assessment provides an indication of the mechanism by which the oxygen consumption is reduced, wherein an increase in $P_{50}$ is associated with competitive inhibition by nitric oxide, and wherein a reduced $VO_{2,max}$ without a significant alteration in $P_{50}$ is associated with a non-competitive inhibition by toxins.

13. The method according to claim 8, wherein the assessment of mitochondrial function is in vivo and further comprises an assessment of mitochondrial outer membrane integrity and intracellular ATP availability, wherein said assessment of mitochondrial outer membrane integrity and intracellular ATP availability comprises steps wherein ALA is administered and kinetics of prompt PpIX fluorescence are measured.

14. The method according to claim 1, wherein an elevated mitochondrial oxygen consumption well above normal values indicates mitochondrial uncoupling and wherein a low mitochondrial oxygen consumption indicates mitochondrial dysfunction.

15. The method of claim 1, wherein the method comprises estimating the rate of extension of said lifetime as an indicator of oxygen consumption, said assessment provides information on the maximal oxygen consumption $VO_{2,max}$.

16. The method of claim 1, wherein the step of repetitively or continuously measuring the lifetime of the first excited triplet state (TAUT1) of endogenous protoporphyrin IX (PpIX) in mitochondria in cells of said tissue is performed using a device for measurement of mitochondrial function, the device comprising:

an excitation light source directed to illuminate a sample volume of said tissue;

a light detector arranged to detect fluorescence or other luminescence from said sample volume or absorption by said sample volume; and a control unit configured to obtain repetitive or continuous measurements of mitochondrial oxygen tension, wherein the control unit is configured to use the measurements after the step of restricting or ceasing the supply of oxygen to said tissue to deduce the Michaelis-Menten constant and/or the maximal oxygen consumption of the mitochondrial respiratory chain in said tissue.

17. The method of claim 16, whereby the temperature of the tissue is regulated.

18. The method of claim 16, whereby the temperature of the tissue is regulated to a value in the range of 35-44° C.

19. The method of claim 16, whereby the at least two measurements are performed by using an excitation light source illuminating said sample volume with blue (~410 nm), green (~510 nm) or red (~632 nm) light and by using a light detector for detecting delayed fluorescence at 630-710 nm.

20. The method of claim 1, whereby the temperature of the tissue is regulated to a value in the range of 35-44° C.

21. The method of claim 1, whereby the lifetime of the first excited triplet state (TAUT1) of endogenous protoporphyrin IX is determined by photo excitation with blue (~410 nm), green (~510 nm) or red (~632 nm) light and detecting delayed fluorescence at 630-710 nm.

* * * * *